United States Patent [19]

Anderson et al.

[11] 4,226,802

[45] Oct. 7, 1980

[54] 2-(4-TRIFLUOROMETHYL-PHENYLAMINO)-3-METHYLBUTANOIC ACID ESTERS AND INTERMEDIATES THEREFOR

[75] Inventors: Richard J. Anderson; Ted A. Baer, both of Palo Alto, Calif.

[73] Assignee: Zoecon Corporation, Palo Alto, Calif.

[21] Appl. No.: 89,003

[22] Filed: Oct. 29, 1979

[51] Int. Cl.³ .............. C07C 101/447; C07C 103/28; C07C 119/20; C07C 121/78

[52] U.S. Cl. .................... 260/465 E; 260/453 RW; 260/465 D; 260/558 A; 560/43; 562/456

[58] Field of Search ........ 260/465 E, 453 RW, 558 A; 560/43

[56] References Cited

U.S. PATENT DOCUMENTS 4,161,537   7/1979   Katsuda et al. .................... 560/43 X

*Primary Examiner*—Dolph H. Torrence
*Attorney, Agent, or Firm*—Donald W. Erickson

[57] ABSTRACT

Synthesis of 2-(4-trifluoromethylphenylamino)-3-methylbutanoic acid and lower alkyl esters thereof, optionally ortho substitution on the phenylamino group, novel intermediates thereof, which are useful intermediates in the synthesis of pesticides.

10 Claims, No Drawings

2-(4-TRIFLUOROMETHYLPHENYLAMINO)-3-METHYLBUTANOIC ACID ESTERS AND INTERMEDIATES THEREFOR

This invention relates to the synthesis of 2-(4-trifluoromethylphenylamino)-3-methylbutanoic acid and lower alkyl esters thereof, optionally substituted at the ortho position of the phenylamino group, and novel intermediates therefor, which are useful in the synthesis of pesticides. More particularly, 2-(4-trifluoromethylphenylamino)-3-methylbutanoic acid and ortho derivatives thereof such as 2-(2-chloro-4-trifluoromethylphenylamino)-3-methylbutanoic acid are useful intermediates in the synthesis of the α-cyano-3-phenoxybenzyl esters thereof which are useful insecticides and acaricides as described by C. A. Henrick and B. A. Garcia, Offenlengungsschrift 28 12 169.

The synthesis of the present invention can be illustrated as follows:

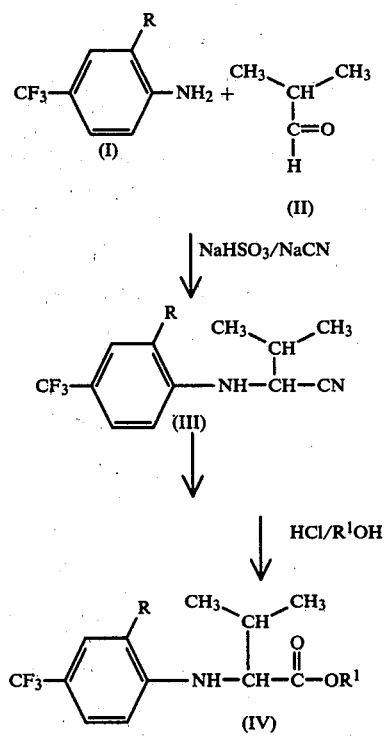

In the above formulas R is hydrogen, bromo, chloro, fluoro or methyl and $R^1$ is lower alkyl of one to three carbon atoms.

In the practice of the above outlined synthesis, the p-trifluoromethylphenylamine (I, R is hydrogen) or the corresponding ortho substituted compound, is reacted with the bisulfite addition product of isobutyraldehyde (II) in an aqueous reaction medium, at a temperature above room temperature, followed by addition of sodium cyanide or potassium cyanide in aqueous medium to form the desired nitrile (III). The nitrile (III) on treatment with HCl or other strong acid in an alcohol such as methanol forms the ester (IV). The reaction can be run generally at room temperature or above. In the treatment of nitrile (III) with HCl or other strong acid there is formed the salt of the iminoether (V) as an intermediate. The iminoether (V) can be isolated by stopping the reaction and working up under basic conditions or it may be permitted to remain in solution and the reaction continued uninterrupted to form the ester (IV). Along with formation of the ester (IV) there is obtained some of the amide (VI). The ester (IV) and the amide (VI) can be converted into the acid, or salt thereof, for use in preparing the pesticidally active 3-phenoxybenzyl esters.

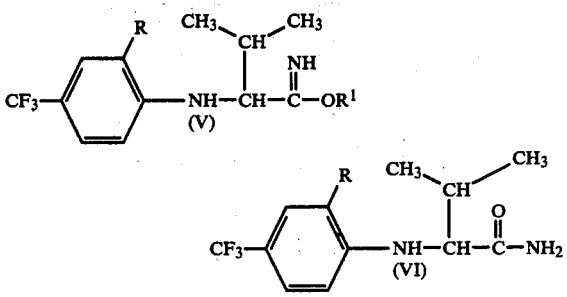

In place of using an ortho substituted amine of formula I as the starting material, the ortho substituent can be introduced following formation of the nitrile (III). For example, the nitrile (III, R is hydrogen) on reaction with, for example, N-chlorosuccinimide or N-bromosuccinimide, in organic solvent gives the ortho chloro or bromo substituted nitrile (III, R is chloro or bromo) which is then converted into the ester (IV) or above.

The following examples are provided to illustrate the practice of the present invention. Temperature is given in degrees centigrade.

EXAMPLE 1

To 7.2 g (0.10 mol) of isobutyraldehyde in 10 ml. of water is added 10.4 g. (0.10 mol) of sodium bisulfite in 20 ml. of water. After about 30 minutes, 16.1 g. (0.1 mol) 4-aminobenzotrifluoride is added along with 10 ml. of water. The mixture is heated to about 70° for 30 minutes and then 4.9 g (0.1 mol) of sodium cyanide in 20 ml. of water is added. The mixture is maintained at 70° for about 7.5 hours and then stirred overnight at room temperature. The solid product is separated by filtration and air dried. An ether solution of this solid is then filtered to remove inorganic material. The ether is removed by evaporation to yield the nitrile (III; R is hydrogen).

EXAMPLE 2

To a solution of 484 mg (2 mmol) of 3-methyl-2-(4-trifluoromethylphenylamino)butyronitrile (III; R is hydrogen) in 5 ml. of carbon tetrachloride is added 267 mg. (2 mmol) of N-chlorosuccinimide. The mixture is heated at 65°. After about 48 hours, the mixture is poured into water and ether. The organic fraction is separated, washed with water, and brine, dried over sodium sulfate, and solvent removed to give 3-methyl-2-(2-chloro-4-trifluoromethylphenylamino)butyronitrile (III; R is chloro).

EXAMPLE 3

To a solution of 276 mg (1.0 mmol) of the nitrile (III; R is chloro) of Example 2 in 4 ml. of methanol at room temperature is added gaseous HCl. The temperature is raised to 40° and the solution stirred overnight. Then the temperature was raised to 60° and additional HCl bubbled through the solution for about 20 minutes. The solution was maintained at about 60° overnight with stirring. The solution was cooled and then poured into ether and 2 M sodium carbonate. The organic phase was separated, washed with brine, dried over sodium sulfate, and solvent removed.

The product is applied to a preparatory SiO₂ plate which is developed in 22% ethyl acetate/hexane to yield methyl 2-(2-chloro-4-trifluoromethylphenylamino)-3-methylbutanoate and, as the lower band, a smaller amount, of 2-(2-chloro-4-trifluoromethylphenylamino)-3-methylbutyramide (VI; R is chloro).

The ester, methyl 2-(2-chloro-4-trifluoromethylphenylamino)-3-methylbutanoate is converted into the acid, 2-(2-chloro-4-trifluoromethylphenylamino)-3-methylbutanoic acid, by treatment with one equivalent of KOH in ethanol/water (9:1) at room temperature.

EXAMPLE 4

A mixture of 2-(2-chloro-4-trifluoromethylphenylamino)-3-methylbutyramide (1 mmol) and 4 ml of methanol, saturated with HCl gas, is heated at 75° for about 40 hours. The mixture is cooled, poured into saturated aqueous sodium bicarbonate and extracted with ether. The combined ether extracts are dried over sodium sulfate and solvent removed in vacuo to yield methyl 2-(2-chloro-4-trifluoromethylphenylamino)-3-methylbutanoate, which can be further purified by prep. thin layer chromatography.

EXAMPLE 5

To 7.2 g (0.1 mol) of isobutyraldehyde in 10 ml of water is added 10.4 g (0.1 mol) of NaHSO₃ in 30 ml of water. The mixture is heated to 50° for 20 minutes and then 16.1 g of p-aminobenzotrifluoride is added, followed by sodium cyanide (0.1 mol) in water. The mixture is heated at 55° for two hours and then cooled and extracted with ether. The ether extracts are washed with water and brine, dried over sodium sulfate and solvent stripped. The crude product is chromatographed on silica developing with ether/hexane (1/1) to give 2-(4-trifluoromethylphenylamino)-3-methylbutylnitrile (III; R is hydrogen), recrystallized from ether/hexane, white solid, m.p. 63.2°–64.8°.

A mixture of 3.63 g (0.015 mol) of the above nitrile, 10 ml of conc. H₂SO₄ and 0.5 ml of water, under nitrogen, is allowed to stand at room temperature for about 24 hours. The mixture is poured onto about 40 g of ice and extracted with ether. The ether extracts are washed with water and brine, dried over sodium sulfate and solvent removed to give 2-(4-trifluoromethylphenylamino)-3-methylbutyramide (VI; R is hydrogen), which can be recrystallized from ether/hexane, m.p. 93°–94°.

EXAMPLE 6

Following the procedure of Example 1, each of 3-chloro-4-aminobenzotrifluoride and 3-fluoro-4-aminobenzotrifluoride is reacted with isobutyraldehyde and sodium cyanide to give the respective nitrile—2-(2-chloro-4-trifluoromethylphenylamino)-3-methylbutylnitrile (III; R is chloro) and 2-(2-fluoro-4-trifluoromethylphenylamino)-3-methylbutylnitrile (III; R is fluoro).

EXAMPLE 7

Following the procedure of Example 3, 2-(4-trifluoromethylphenylamino)-3-methylbutylnitrile (III; R is hydrogen) is heated in HCl/methanol to give a mixture of methyl 2-(4-trifluoromethylphenylamino)-3-methylbutanoate and 2-(4-trifluoromethylphenylamino)-3-methylbutyramide, which are separated using prep. thin layer chromatography developing with ethyl acetate/hexane.

EXAMPLE 8

A solution of 276 mg (1.0 mmol) of 2-(2-chloro-4-trifluoromethylphenylamino)-3-methylbutyronitrile in 3 ml of dry methanol (dried over molecular sieves) at 60° is saturated with gaseous HCl (HCl bubbled into the solution for about 45 minutes). Temperature is raised to 80° after 4 hours and continued for about 92 hours. After cooling, the mixture is poured into 2 M Na₂CO₃ and ether. The organic phase is separated, washed with brine, dried over Na₂SO₄ and solvent removed to give methyl 2-(2-chloro-4-trifluoromethylphenylamino)-3-methylbutanoate and 2-(2-chloro-4-trifluoromethylphenylamino)-3-methylbutryamide in a ratio of about 98.1 to 1.9, respectively.

EXAMPLE 9

A solution of 1 mmol of 2-(2-chloro-4-trifluoromethylphenylamino)-3-methylbutyronitrile in 3 ml of dry methanol at 60° is saturated with gaseous HCl. Temperature is raised to 80° for about 2 hours. After cooling, the mixture is poured into ether and aqueous NaHCO₃. The organic phase is separated, washed with brine, dried over Na₂SO₄ and solvent removed to give the iminoether (V; R is chloro, R¹ is methyl), which is plated using prep. thin layer chromatography.

What is claimed is:

1. A compound of the following formula:

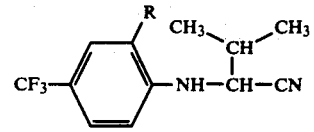

wherein R is hydrogen, bromo, chloro, fluoro or methyl.

2. The compound according to claim 1 wherein R is hydrogen.

3. The compound according to claim 1 wherein R is chloro.

4. The compound according to claim 1 wherein R is fluoro.

5. A compound of the formula:

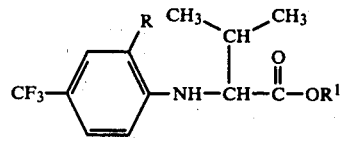

wherein R is hydrogen, bromo, chloro, fluoro or methyl and R¹ is lower alkyl or one to three carbon atoms.

6. A compound according to claim 5 wherein R is hydrogen and R¹ is methyl.

7. A compound according to claim 5 wherein R is chloro and R¹ is methyl.

8. A compound according to claim 5 wherein R is fluoro and R¹ is methyl.

9. A compound of the formula:

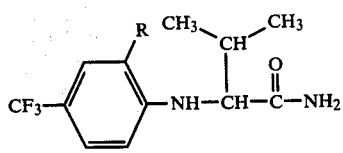
wherein R is hydrogen, bromo, chloro, fluoro or methyl.
10. A compound of the formula:
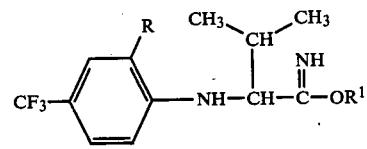
wherein R is hydrogen, bromo, chloro, fluoro or methyl and $R^1$ is lower alkyl of one to three carbon atoms.
* * * * *